(12) United States Patent
He et al.

(10) Patent No.: US 11,285,161 B2
(45) Date of Patent: Mar. 29, 2022

(54) METHOD AND COMPOSITION FOR TREATING MENTAL DISORDER AND PAIN ASSOCIATED WITH NERVE DAMAGE

(71) Applicant: City University of Hong Kong, Kowloon (HK)

(72) Inventors: Jufang He, Kowloon (HK); Xu Zhang, Kowloon (HK); Hemin Feng, Kowloon (HK); Ge Zhang, Kowloon (HK); Shenghui Xu, Kowloon (HK); Sarah Hau, Kowloon (HK)

(73) Assignee: City University of Hong Kong, Kowloon (HK)

( * ) Notice: Subject to any disclaimer, the term of this patent is extended or adjusted under 35 U.S.C. 154(b) by 95 days.

(21) Appl. No.: 16/395,499

(22) Filed: Apr. 26, 2019

(65) Prior Publication Data

US 2020/0338089 A1    Oct. 29, 2020

(51) Int. Cl.
| | |
|---|---|
| *A61K 31/5513* | (2006.01) |
| *A61K 45/06* | (2006.01) |
| *A61P 29/02* | (2006.01) |
| *A61P 25/24* | (2006.01) |
| *A61K 9/00* | (2006.01) |

(52) U.S. Cl.
CPC ........ *A61K 31/5513* (2013.01); *A61K 9/0019* (2013.01); *A61K 45/06* (2013.01); *A61P 25/24* (2018.01); *A61P 29/02* (2018.01)

(58) Field of Classification Search
CPC .. A61K 31/5513; A61K 45/06; A61K 9/0019; A61P 29/02; A61P 25/24
USPC ........................................................ 514/221
See application file for complete search history.

(56) References Cited

U.S. PATENT DOCUMENTS

| | | | |
|---|---|---|---|
| 5,153,191 A | 10/1992 | Woodruff | |
| 5,217,957 A | 6/1993 | Woodruff | |
| 2005/0042283 A1* | 2/2005 | Wang | A61K 31/426 424/464 |

FOREIGN PATENT DOCUMENTS

| | | |
|---|---|---|
| WO | 9211246 | 7/1992 |
| WO | 9501964 | 1/1995 |
| WO | 9506040 | 3/1995 |
| WO | 02092096 | 11/2002 |
| WO | 2005007107 | 1/2005 |
| WO | 2006044352 | 4/2006 |
| WO | 2015077572 | 5/2015 |
| WO | 2016020698 | 2/2016 |

OTHER PUBLICATIONS

Becker et al Molecular Psychiatry, 2018, 13, 1079-1092 (Year: 2018).*
Cryan et al., Neuroscience and Biobehavioral Reviews, 2005, 29, 571-625 (Year: 2005).*
C Becker, et al, "Repeated social defeat-induced depression-like behavioral and biological alterations in rats: involvement of cholecystokinin", Molecular Psychiatry (2008) 13, 1079-1092.
Fernando Hernando, et al, "The CCKB receptor antagonist, L-365,260, elicits antidepressant-type effects in the forced-swim test in mice", European Journal of Pharmacology 261 (1994) 257-263.
Fernando Hernando, et al, "Antidepressant-like effects of CCKB receptor antagonists: involvement of the opioid system", European Journal of Pharmacology 318 (1996) 221-229.

* cited by examiner

*Primary Examiner* — Yevgeny Valenrod
(74) *Attorney, Agent, or Firm* — Renner Kenner Greive Bobak Taylor & Weber

(57) ABSTRACT

A method of treating a subject suffering from mental disorder including the step of administering an effective amount of a cholecystokinin-2 receptor antagonist or a pharmaceutical acceptable salt thereof to the subject. A method of treating a subject suffering from pain associated with nerve injury including the step of administering an effective amount of a cholecystokinin-2 receptor antagonist or a pharmaceutical acceptable salt thereof to the subject. A pharmaceutical composition including the cholecystokinin-2 receptor antagonist or a pharmaceutical acceptable salt thereof as active ingredient, one or more antidepressant compounds, and a pharmaceutically acceptable excipient.

13 Claims, 3 Drawing Sheets

METHOD AND COMPOSITION FOR TREATING MENTAL DISORDER AND PAIN ASSOCIATED WITH NERVE DAMAGE

TECHNICAL FIELD

The present invention relates to a method of treating mental disorder, particularly depression, in a subject in particular, but not exclusively, by administering a cholecystokinin (CCK) receptor antagonist to the subject. The present invention also relates to a method of treating pain associated with nerve injury in a subject by administering a cholecystokinin (CCK) receptor antagonist to the subject. The invention also relates to a pharmaceutical composition for said methods.

BACKGROUND OF THE INVENTION

Mental disorders encompass a wide range of neuropsychiatric disorders. Depression is a mental disorder that refers to a wide range of mental health problems characterized by the absence of a positive effect, including for example, loss of interest and enjoyment in ordinary pursuits, pleasures and experiences that would ordinarily be enjoyed. Depression may also be characterized by low moods and a range of associated emotional, cognitive, physical and behavioral symptoms. Between 4-10% of people worldwide are likely to experience major depression in their lifetime, and about 2.5-5% are likely to experience dysthymia (low grade chronic depressive symptoms) with disparities attributable to geographical differences and method of assessment (Waraich et al., 2004).

Antidepressant drugs that are currently available on the market may be classified as selective serotonin reuptake inhibitors (SSRIs), monoamine oxidase inhibitors (MAOIs), tricyclic antidepressants, atypical antidepressants, and selective serotonin and norepinephrine reuptake inhibitors (SNRIs), with SSRIs most commonly and widely used. However, common side effects associated with use of SSRIs include nausea, tremors, nervousness, insomnia and sexual problems. Accordingly, there remains a strong need for novel and effective approach in treating mental disorders such as depression.

SUMMARY OF THE INVENTION

In this invention, the inventors unexpectedly found that cholecystokinin-2 (CCK2) receptor antagonist are useful in treating mental disorder and pain associated with nerve injury. In contrast to the known mechanism which activates the CCK receptors as described in *Neuroscience Letter*, 1981, 24(2): 175-180, it was found that the inhibition on CCK2 receptors of the present invention can effectively treat major and minor forms of depression and alleviate pain.

In a first aspect, the present invention provides a method of treating a subject suffering from mental disorder comprising the step of administering an effective amount of a CCK2 receptor antagonist to the subject.

The CCK2 receptor antagonist administered according to the present invention has a structure of Formula (Ia) including any pharmaceutical acceptable salt thereof:

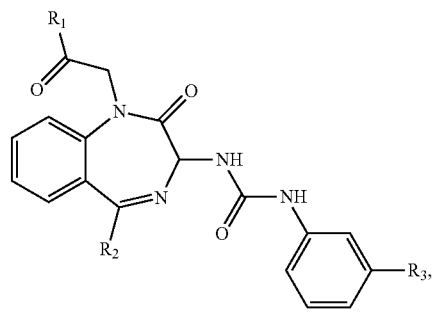

Formula (Ia)

wherein $R_1$ and $R_2$ are independently a hydrogen atom, a substituted or unsubstituted linear or branched chain C1 to C5 alkyl group, a substituted or unsubstituted aryl group, or a heteroaryl; and $R_3$ is a hydrogen atom, a substituted or unsubstituted linear or branched chain C1 to C3 alkyl group, or a C1 to C3 alkylamino group.

In particular, the CCK2 receptor antagonist has a structure of Formula (Ia) with $R_1$ being a linear or branched chain $C_1$ to C4 alkyl group, or a substituted or unsubstituted aryl group; $R_2$ being a substituted or unsubstituted aryl group, or a heteroaryl; and $R_3$ being a methyl group, an ethyl group, a methylamino group or an ethylamino group.

Preferably, the CCK2 receptor antagonist has a structure of Formula (IIa) or Formula (IIIa):

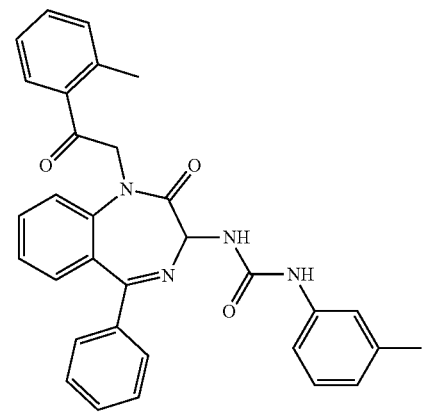

Formula (IIa)

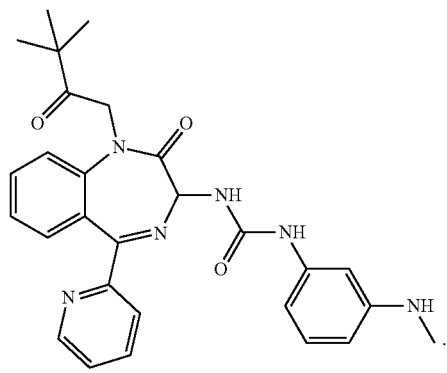

Formula (IIIa)

More preferably, the CCK2 receptor antagonist has a structure of Formula (IIb) or Formula (IIIb):

Formula (IIb)

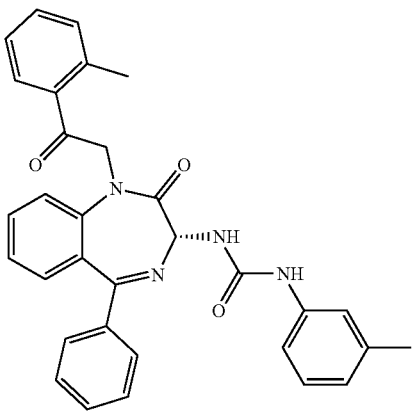

Formula (IIIb)

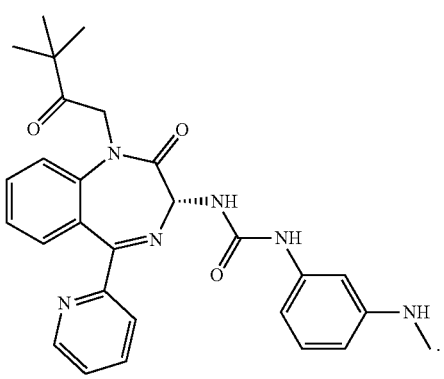

In an embodiment, the CCK2 receptor antagonist is administered in combination with one or more antidepressant compounds to the subject. In particular, the antidepressant compound is selected from the group consisting of citalopram, escitalopram, paroxetine, fluoxetine, sertraline, selegiline, isocarboxzaid, parnate, tranylcypromine, imitriptyline, amoxapine, desipramine, doxepin, imipramine, nortriptyline, protriptyline, trimipramine, maprotiline, trazodone, nefazodone, mirtazapine, bupropion, venlafaxine, duloxetine, and desvenlafaxine.

In an embodiment, the CCK2 receptor antagonist is administered to the subject via injection.

In a second aspect, the present invention provides a method of treating a subject suffering from pain associated with a nerve injury comprising the step of administering an effective amount of a CCK2 receptor antagonist as described above to the subject. In particular, the subject is suffering from chronic pain.

In a third aspect, the present invention pertains to a pharmaceutical composition comprising a CCK2 receptor antagonist as described above, or a pharmaceutical acceptable salt thereof as active ingredient and one or more antidepressant compounds. Preferably, the antidepressant compound is selected from the group consisting of citalopram, escitalopram, paroxetine, fluoxetine, sertraline, selegiline, isocarboxzaid, parnate, tranylcypromine, imitriptyline, amoxapine, desipramine, doxepin, imipramine, nortriptyline, protriptyline, trimipramine, maprotiline, trazodone, nefazodone, mirtazapine, bupropion, venlafaxine, duloxetine, and desvenlafaxine.

Particularly, the inventor found that the benzodiazepine compounds, i.e. compound of Formula (IIb) and Formula (IIIb) (each referred as YM022 and YF476 respectively) can selectively inhibit CCK2 receptors. These two compounds are generally applied in the treatment and/or prevention of gastric and duodenal ulceration, gastritis, reflux esophagitis, Zollinger-Ellison syndrome, osteoporosis, neuroendocrine tumors and digestive system tumors, but not mental disorders, particularly depression, or the treatment of pain. The experimental results of the present invention indicate that YM022 and YF476 can significantly treat major and minor forms of depression and alleviate pain.

In addition, it is found that these compounds have a long half-life in vivo, providing antidepressant and analgesic effects. In particular, a single subcutaneous administration of these compounds is capable of resulting in a high circulating concentration of the compounds in vivo for as long as 8 weeks whilst antidepressants currently used clinically require to be taken at least once daily to achieve a similar goal. Accordingly, it is believed that these compounds are effective in treating mental disorder and pain, and may be further applied in the development of medicament for treating refractory depression and refractory pain.

Those skilled in the art will appreciate that the invention described herein is susceptible to variations and modifications other than those specifically described. The invention includes all such variations and modifications. The invention also includes all steps and features referred to or indicated in the specification, individually or collectively, and any and all combinations of the steps or features.

Other features and aspects of the invention will become apparent by consideration of the following detailed description and accompanying drawings.

DETAILED DESCRIPTION OF THE EMBODIMENTS

Figure 1:
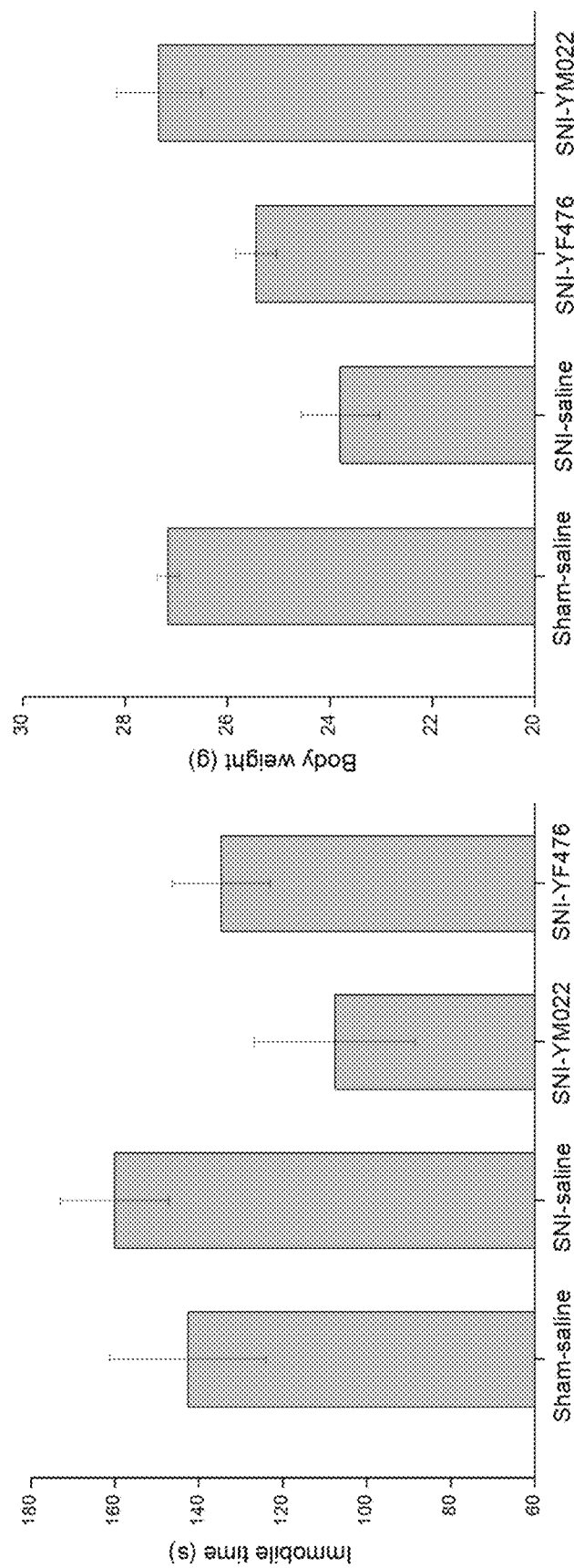
FIG. 1A is a bar chart showing the effect of treatment with the compound of Formula (IIb) or the compound of Formula (IIIb) (referred to as YM022 and YF476 respectively, 0.3 µg/kg) on immobile time (seconds) in tail suspension tests of spared nerve injury (SNI) mice 40 days after SNI surgery and 10 days after discontinuation of YM022 and YF476 (expressed as mean±SEM). In the Sham group, the sciatic nerves (sural, common peroneal, tibial nerves) were dissected but not cut.
FIG. 1B is a bar chart showing the effect of treatment with compounds YM022 or YF476 (0.3 µg/kg) on body weight (grams) in SNI mice 40 days after SNI surgery and 10 days after discontinuation of YM022 or YF476 (expressed as mean±SEM).

Unless otherwise defined, all technical terms used herein have the same meaning as commonly understood by one skilled in the art to which the invention belongs.

As used herein, "comprising" means including the following elements but not excluding others. "Consisting of" means that the material solely consists of, i.e. is formed by the respective element. As used herein, the forms "a," "an," and "the", are intended to include the singular and plural forms unless the context clearly indicates otherwise.

The present invention in a first aspect provides a method of treating a subject suffering from mental disorder. The method comprises a step of administering an effective amount of a cholecystokinin-2 (CCK2) receptor antagonist to the subject. The term "CCK receptor antagonist" used herein generally refers to a specific type of receptor antagonist that blocks the receptor sites for the peptide hormone CCK. It is appreciated in the art that there are two subtypes of receptor, namely CCK1 receptor and CCK2 receptor (also known as CCK A receptor and CCK B receptor). The CCK receptor antagonist is defined by its selectivity towards each subtype of receptor, namely CCK1 receptor antagonist and CCK2 receptor antagonist.

The CCK2 receptor antagonist of the present invention may be a modified peptide molecule or a non-peptide molecule.

In an embodiment, the CCK2 receptor antagonist has a structure of Formula (Ia):

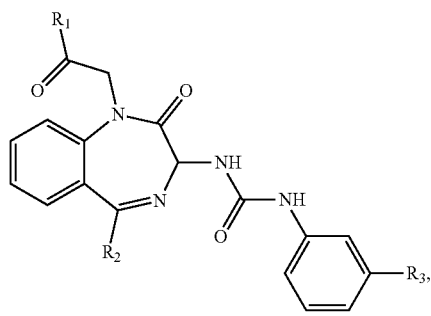

Formula (Ia)

wherein $R_1$ and $R_2$ are independently a hydrogen atom, a substituted or unsubstituted linear or branched chain C1 to C5 alkyl group, a substituted or unsubstituted aryl group, or a heteroaryl; and $R_3$ is a hydrogen atom, a substituted or unsubstituted linear or branched chain C1 to C3 alkyl group, or a C1 to C3 alkylamino group.

It has been found that the CCK2 receptor antagonist having the Formula (Ia) or preferably Formula (Ib) below is exceptionally well suited to the treatment of mental disorder.

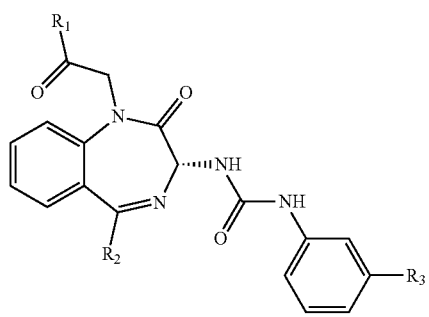

Formula (Ib)

wherein $R_1$, $R_2$ and $R_3$ are as defined above.

In particular, $R_1$ is a linear or branched C1 to C4 alkyl group such as methyl, ethyl, propyl, butyl, isopropyl, tert-butyl, or an unsubstituted aryl group such as phenyl, or a substituted aryl group such as tolyl, xylyl, naphthyl, halophenyl, thiophenyl, or aminophenyl. $R_2$ is the aforementioned substituted or unsubstituted aryl group, or a heteroaryl group such as pyridyl, pyrimidinyl, thienyl, imidazopyridyl, or pyrazolyl. $R_3$ is a methyl, an ethyl, a methylamino, or an ethylamino group.

In a preferred embodiment, the CCK2 receptor antagonist has a structure of Formula (IIa) or Formula (IIIa):

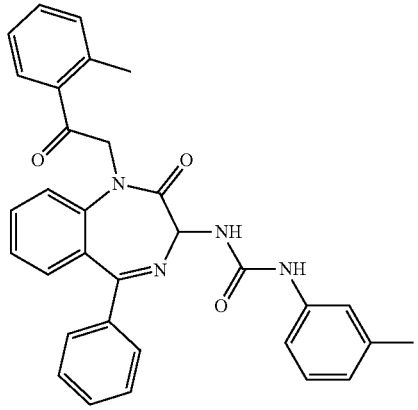

Formula (IIa)

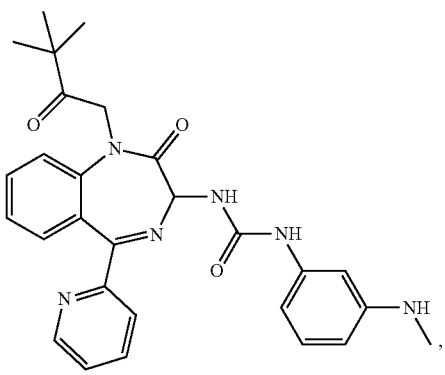

Formula (IIIa)

including any pharmaceutically acceptable, solvate or anhydrate thereof and including any stereoisomer, diastereomer, enantiomer or racemate thereof.

In particular, the CCK2 receptor antagonist has a structure of Formula (IIb) or Formula (IIIb)

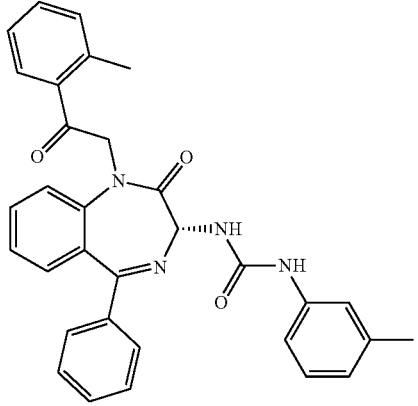

Formula (IIb)

Formula (IIIb)

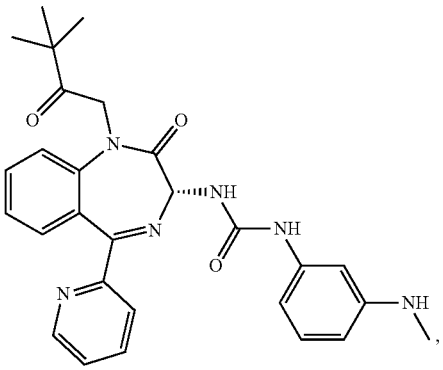

including any pharmaceutically acceptable, solvate or anhydrate thereof. The compound of Formula (IIb) is known as YM022 whereas the compound of Formula (IIIb) is known as YF476. These compounds may be prepared or obtained according to suitable methods.

YM022 has an $IC_{50}$ of 63 nM to the CCK1 receptor and an $IC_{50}$ of 0.07 nM to the CCK2 receptor. YF476 has an $IC_{50}$ of 0.5 μM to the CCK1 receptor and an $IC_{50}$ of 0.11 nM to the CCK2 receptor. YM022 and YF476 have antagonistic effects on the CCK1 and CCK2 receptor, and selectively inhibit CCK2 receptors. The CCK2 receptor antagonists of the present invention exhibit stable and prolonged pharmacological effects. Advantageously, the CCK2 receptor antagonists of the present invention have a prolonged half life in vivo and may be used as an efficient and long-acting treatment for mental disorders.

In an alternative embodiment, the CCK2 receptor antagonist may be a molecule selected from the group consisting of: proglumide, CI-988, CI-1015, L-365260, L-369293, RP-69758, LY-255910, LY288513, PD-135158, PD-145942, and a derivative thereof.

Also contemplated by the present invention are any pharmaceutically acceptable salts, hydrates, solvates, anhydrates as well as enantiomers and their mixtures, stereoisomeric forms, racemates, diastereomers and their mixtures of the CCK2 receptor antagonist of the present invention.

The term "solvate" refers to a complex of variable stoichiometry formed by a solute, i.e. the CCK2 receptor antagonist, and a solvent. If the solvent is water, the solvate formed is a hydrate. As used herein, the term "anhydrate" means any compound free of the water of hydration, as would be understood in the art. Suitable pharmaceutically acceptable salts are those which are suitable to be administered to subjects, in particular mammals such as humans and can be prepared with sufficient purity and used to prepare a pharmaceutical composition. The terms stereoisomers, diastereomers, enantiomers and racemates are known to the skilled person.

"Treating" the mental disorder in particular includes any treatment of a mental disorder including inhibiting, improving or providing relief of the symptoms, reducing the incidence of the symptoms or arrest of the development of the symptoms that directly or indirectly manifest as a result of the mental disorder. Treating the mental disorder may also include prevention of the onset and/or progression of the mental disorder.

The term "mental disorder" refers to a neuropsychiatric disorder in which a subject suffers from a singular, a combination of, or a breadth of emotional, cognitive, physical and/or behavioral symptoms. The term "mental disorder" herein is not intended to imply a distinction between "physical" and "mental" disorders and considered to encompass the full breadth of these disorders. It is appreciated in the art that there are various classes of mental disorders, including but not limited to, neurodevelopmental disorders, psychotic disorders, bipolar and related disorders, anxiety disorders, trauma- and stressor-related disorders, mood disorders or depressive disorders. The mental disorder may include more than one neuropsychiatric disorder. In a preferred embodiment, the mental disorder is a depressive disorder. In a most preferred embodiment, the mental disorder is depression.

Depression as discussed herein refers to a wide range of mental health problems that negatively impacts the way a subject feels, thinks or acts and can be characterized by depressed moods or feelings of sadness or a loss of interest and enjoyment in activities and experiences once enjoyed. Symptoms can include one or more of a depressed mood, loss of interest, change in appetite, including weight loss or weight gain, changes in sleeping patterns, loss of energy or increased fatigue, difficulty concentrating or making decisions or an increase in purposeless physical activity. Depression as described herein incorporates various types of depression including but not limited to major depression, dysthymia, atypical depression, post-partum depression.

In an embodiment herein, the administration of the CCK2 receptor antagonist to the subject can produce stable relief from depressive disorders, particularly depression, in the subject with a prolonged effect.

The expression "effective amount" generally denotes an amount sufficient to produce therapeutically desirable results, wherein the exact nature of the result varies depending on the specific disorder which is treated. The CCK2 receptor antagonist of the present invention may be contained in a composition, in particular a pharmaceutical composition, in an effective amount, i.e. an amount suitable to treat or prevent depression in a subject, in particular a mammal.

The subject can be a human or animal, in particular the subject is a mammal, preferably a human. The subject is, thus, preferably a human suffering from a mental disorder, particularly depression. The subject may also include a human having resistance to conventional antidepressant drugs, i.e. the subject may have refractory depression.

The effective amount of the CCK2 receptor antagonist of the present invention may depend on the species, body weight, age and individual conditions of the subject and can be determined by standard procedures such as experimental animals. In an embodiment where the subject is a mouse, the effective amount is preferably about 0.001 mg/kg, 0.01 mg/kg, 0.1 mg/kg, 1 mg/kg, 10 mg/kg, 100 mg/kg or 500 mg/kg. The effective amount of the CCK2 receptor antagonist may be indicated by a reduction in the severity or incidence of symptoms of depression of the subject over a defined period of time.

A skilled person may be aware of determining whether a subject is in need of treatment for mental disorder or treatment for depression according to the present invention based on predisposing factors. The term "predisposing factors" refers to factors or conditions that render a subject vulnerable to a disease or disorder, i.e. mental disorder or depression in the present disclosure. Predisposing factors for mental disorder, particularly depression, may include but are not limited to, family genetic factors; sleep disorders such as chronic sleep problems; chronic conditions such as chronic pain, arthritis, Parkinson's disease, multiple sclerosis, cancer among others that can be linked to higher rates of depression; substance abuse or certain medications; or social factors that include, for example, abuse or lack of social support.

In an embodiment, the CCK2 receptor antagonist of the present invention may be administered in combination with an effective amount of one or more antidepressant compounds. The term "antidepressant compound" includes drugs which are commonly administered to a subject having no resistance to the current antidepressant drug therapy, i.e. compounds which have been known to be used in the treatment of depression.

In particular, the antidepressant compound is selected from the group consisting of citalopram, escitalopram, paroxetine, fluoxetine, sertraline, selegiline, isocarboxzaid, parnate, tranylcypromine, imitriptyline, amoxapine, desipramine, doxepin, imipramine, nortriptyline, protriptyline, trimipramine, maprotiline, trazodone, nefazodone, mirtazapine, bupropion, venlafaxine, duloxetine, and desvenlafaxine.

The antidepressant compound may be administered before, after or simultaneously with the CCK2 receptor antagonist, in particular before or simultaneously with the CCK2 receptor antagonist, further preferred simultaneously with the CCK2 receptor antagonist.

The CCK2 receptor antagonist according to the present invention may be administered by an oral, injection, rectal, topical, parenteral, transdermal or inhalation route to a subject. In an embodiment where the subject is a mouse, the CCK2 receptor antagonist is administered through injection to the subject. The term injection encompasses intraperitoneal, intravenous, intramuscular, subcutaneous and intradermal administration. In a preferred embodiment, the CCK2 receptor antagonist is administered to the subject by injection, preferably intravenous or subcutaneous injection.

In the case of oral administration, tablets may contain additions such as sodium citrate, calcium carbonate and dicalcium phosphate together with various additives, such as starch, preferably potato starch, gelatin and the like in addition to the excipients mentioned. Lubricants such as magnesium stearate, sodium lauryl sulphate and talc may additionally be used for tabletting. In the case of aqueous suspensions, various flavor enhancers or colorants may be added to the active compounds in addition to the above-mentioned auxiliaries.

The present invention in a second aspect provides a method of treating a subject suffering from pain associated with nerve injury. The method comprises a step of administering an effective amount of a CCK2 receptor antagonist as described above to the subject.

Advantageously, the CCK2 receptor antagonists of the present invention have a prolonged half life in vivo and may be used as an efficient and long-acting treatment for the treatment of pain associated with nerve injury.

Pain is an unpleasant sensory and emotional experience associated with actual or potential tissue damage, or described in terms of such damage. "Treating" the pain associated with nerve injury includes the reduction or mitigation of the severity, incidence or persistence of pain caused by nerve injury. Pain may refer to acute pain, chronic pain or procedural pain. "Acute pain" refers to sudden pain from a specific cause (injury, infection, inflammation, etc.) that has lasted for a limited period of time whilst "chronic pain" is often associated with long-term incurable or intractable medical conditions or diseases. "Procedural pain" refers to pain arising from a medical, dental surgical or other procedure wherein the procedure may be planned or associated with acute trauma.

In an embodiment herein, the administration of the CCK2 receptor antagonist to the subject can alleviate pain associated with nerve injury. In a preferred embodiment, the pain is chronic pain.

In an embodiment where the subject is a mouse, the effective amount of the CCK2 receptor antagonist for alleviating pain is preferably about 0.001 mg/kg, 0.01 mg/kg, 0.1 mg/kg, 1 mg/kg, 10 mg/kg, 100 mg/kg or 500 mg/kg. The effective amount of the CCK2 receptor antagonist for this method may be indicated by a reduction in the severity or incidence of symptoms of pain of the subject over a defined period of time. It would be appreciated that the effective amount may depends on the species, body weight, age and individual conditions of the subject and can be determined by standard procedures.

In a further embodiment, the CCK receptor antagonist may be administered in the treatment of chronic pain that is refractory in nature, i.e. where conventional therapeutic options for the treatment of chronic pain are ineffective.

The CCK2 receptor antagonist of the present invention may be administered in combination with an effective amount of one or more analgesic compounds. The term "analgesic compound" includes drugs which are commonly administered to a subject having no resistance to the current analgesic drug therapy, i.e. compounds which are known to be used in the treatment of pain.

In an example embodiment, the analgesic compound may be selected from the group consisting of paracetamol, aspirin, ibuprofen, naproxen, diazepam, celecoxib, duloxetine, codeine, fentanyl, oxycodone, methadone, hydromorphone, diflunisal, hydrocodone, acetaminophen, and indomethacin.

In an example embodiment, the CCK2 receptor antagonist may be administered alone or in combination with one or more analgesic compounds to a subject in the form of an epidural injection in the treatment of chronic pain.

In another aspect, the present invention pertains to a pharmaceutical composition comprising a CCK2 receptor antagonist as described above or a pharmaceutical acceptable salt thereof as active ingredient, one or more antidepressant compounds as described above, and optionally a pharmaceutically acceptable excipient.

In yet another aspect, the present invention pertains to a pharmaceutical composition comprising a CCK2 receptor antagonist as described above or a pharmaceutical acceptable salt thereof as active ingredient, one or more analgesic compounds as described above, and optionally a pharmaceutically acceptable excipient.

The "pharmaceutically acceptable excipient" may include pharmaceutically acceptable carriers, diluents, preserving agents, solubilizing agents, stabilizing agents, disintegrating agents, binding agents, lubricating agents, wetting agents, emulsifiers, sweeteners, colorants, odorants, salts, buffers, coating agents and antioxidants. Suitable excipients and techniques for formulating pharmaceutical composition are aware by a skilled person in the art.

Accordingly, the present invention also pertains to use of a CCK2 receptor antagonist as described above in the treatment of mental disorders, particularly depression, and use of the CCK2 receptor antagonist as described above in the preparation of a medicament for treatment of mental disorders, particularly depression.

The present invention further pertains to use of a CCK2 receptor antagonist as described above in the treatment of pain associated with nerve injury, particularly chronic pain, and use of the CCK2 receptor antagonist as described above in the preparation of a medicament for treatment of pain associated with a nerve injury.

Based on the above, it would be appreciated that the CCK2 receptor antagonists of the present invention are useful in treating a subject who is at the same time suffering from mental disorder such as depression and pain such as chronic pain associated with nerve injury.

Advantageously, single administration of the CCK2 receptor antagonist as described above can produce a high circulating concentration of the CCK2 receptor antagonist for as long as 8 weeks, thereby providing effective and stable yet prolonged pharmacological effects.

The experiments as described below further support the antidepressant effect and analgesic properties of the CCK2 receptor antagonist according to the present invention.

EXAMPLES

Example 1

The antidepressant and analgesic activities of the compound of formula (IIb) (referred to as YM022) and the compound of formula (IIIb) (referred to as YF476) were investigated in a mouse model of spared nerve injury (SNI). The SNI model is a partial denervation model in which the injured nerves produce consistent pain hypersensitivity in the territory of the spared sural nerve, wherein the spared nerve injury can provoke depressive-like behaviors. In the experiment, depressive-like behaviors were assessed by a tail suspension test and monitoring body weight. Responses to pain were tested by measuring the sensitivity to mechanical stimulation by von Frey filaments.

Methods

For the SNI surgery, the mice were anesthetized by intraperitoneal injection of ketamine (100 mg/kg) and xylazine (15 mg/kg). The skin on the lateral surface of the left thigh was cleaned and incised, and then sterile scissors were used to expose three branches of the sciatic nerves: namely sural, common peroneal, and tibial nerves. The common peroneal and tibial nerves were tied with non-absorbent 6-0 silk sutures at the point of trifurcation, whereas the sural nerve was untouched. The tied nerves were grabbed below the sutures with a pair of tweezers and cut above and below the tweezers. In the Sham group, these nerves were dissected but not cut. At the end of surgery, muscle and skin layers were closed with sutures in distinct layers.

After SNI surgery (Day 0), the mice were treated with the compound of formula (IIb) (referred to as YM022) and the compound of formula IIIb (referred to as YF476), both at 30 ng/kg, for 24 days (Day 7-Day 30). The bodyweight of the mice were measured (FIG. 1B) and the tail suspension test (FIG. 1A) was carried out on Day 40 to assess the depressive status. In the tail suspension test, each mouse was suspended by its tail and secured by adhesive tape to the suspension bar. A blinded observer monitored the test for 6 min and recorded the immobility time.

As shown in FIG. 1A, treatment with YM022 and YF476 had a significant effect and reduced immobile time (in seconds) when compared with controls SNI-saline and Sham-saline. Treatment with YM022 and YF476 increased body weight in comparison with SNI-saline (FIG. 1B). The antidepressant-type effects of YM022 and YF476 were also still significant even after the administration of drug had discontinued for 10 days (FIG. 1A and FIG. 1B).

Figure 2:
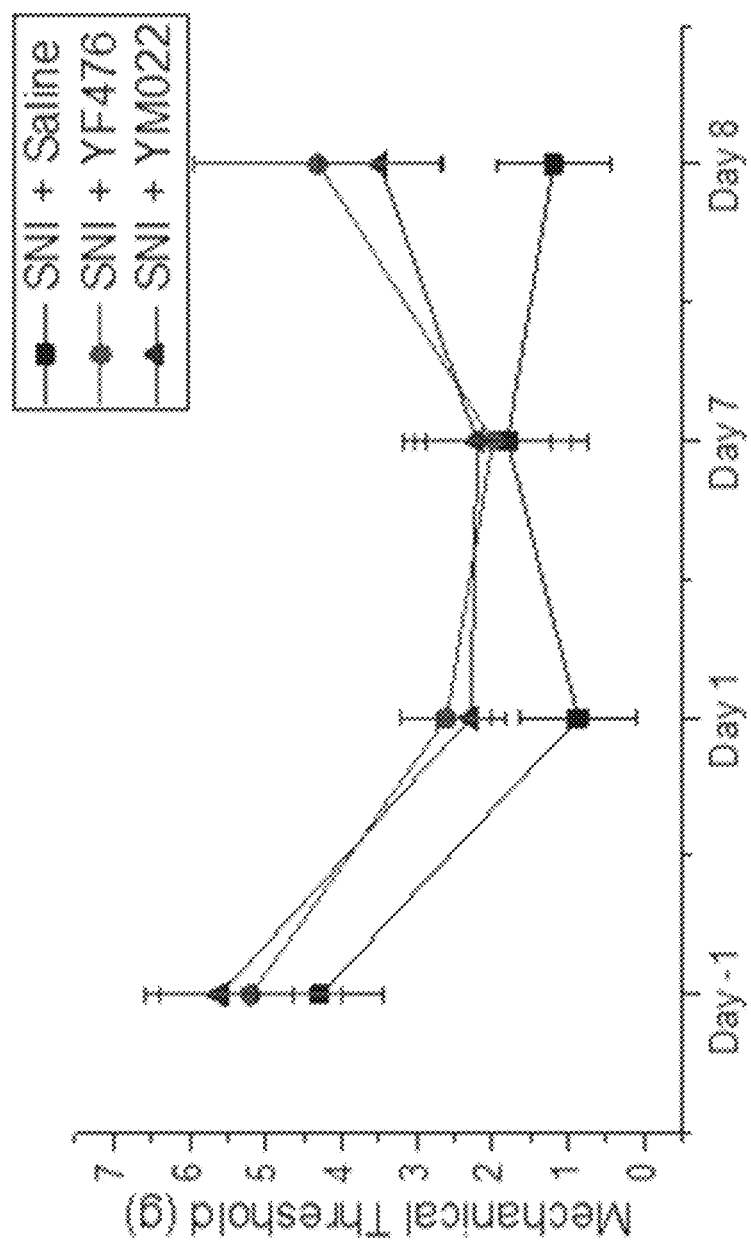
FIG. 2 is a line chart showing the effect of treatment with compounds YM022 or YF476 on the mechanical threshold (grams) of SNI mice in the Von Frey filament test one day before surgery (Day-1), one day (Day 1), seven days (Day 7) or eight days (Day 8) after injection of compound YM022 or YF476.

The Von Frey filament test was used 1 day before the surgery (Day-1) or on Day 1, Day 7 (after drug injection), Day 8 (after drug injection) to estimate the sensitivity of the mice to the mechanical stimulation. For the Von Frey monofilament assay, mice were individually placed in plastic chambers and habituated for 15 minutes prior to the test. Von Frey filaments were used to stimulate the lateral third of left paws of animals initially with the 1.0 g filament but subsequently with logarithmically incremental stiffness from 0.008 to 8.0 g. A positive response was defined by sudden paw withdrawal, sudden flinching, and sudden paw licking, indicating sensation of pain by the mouse. Response in three out of five stimuli was regarded as a positive reaction and the threshold level was recorded (FIG. 2). The analgesic effects were clear from FIG. 2, where treatment with YM022 and YF476 resulted in a higher mechanical threshold being reached on Day 8.

Example 2

Figure 3B:
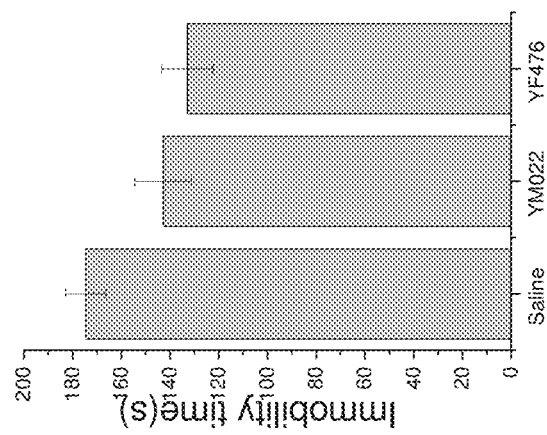
FIG. 3B is a bar chart showing immobile times in an acute forced swimming test for mice treated with saline, compound YF476 (30 µg/kg) or compound YM022 (30 µg/kg) (expressed as mean±SEM).
Figure 3A:
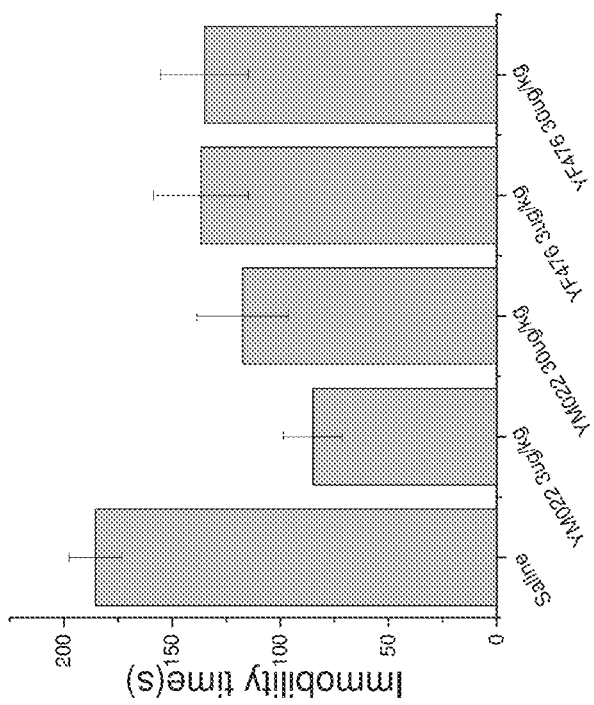
FIG. 3A is a bar chart showing immobile times in an acute tail suspension test for mice treated with saline, compound YF476 (3 µg/kg or 30 µg/kg) or compound YM022 (3 µg/kg or 30 µg/kg) (expressed as mean±SEM).

In another acute tail suspension test, mice were injected intraperitoneally with YM022 (3 µg/kg or 30 µg/kg), YF476 (3 µg/kg or 30 µg/kg) or saline 30 minutes before the test. The tail suspension test was then performed as described above. As shown in FIG. 3A, both the YM022 and YF476 group had less immobile time compared to the saline group, indicating the antidepressant-type effects of YM022 and YF476.

Example 3

In the forced swim test, mice were forced to swim in a narrow cylinder from which they cannot escape. A Plexiglas cylinder (13 cm diameter and 24 cm high) containing water (22° C.±2° C.) to a depth of 10 cm was used. The mice were injected intraperitoneally with YM022 (30 µg/kg), YF476 (30 µg/kg) or saline 30 minutes before the test. After placing the animals in the cylinders, the duration of immobility during the 5-minute test were measured. As shown in FIGS. 3A and 3B, both the YM022 and YF476 group had less immobile time compared to the saline group further confirming the antidepressant-type effects of YM022 and YF476.

The invention claimed is:

1. A method of treating a subject suffering from mental disorder comprising the step of administering an effective amount of a cholecystokinin-2 receptor antagonist or a pharmaceutical acceptable salt thereof to the subject, wherein the cholecystokinin-2 receptor antagonist has a structure of Formula (Ia):

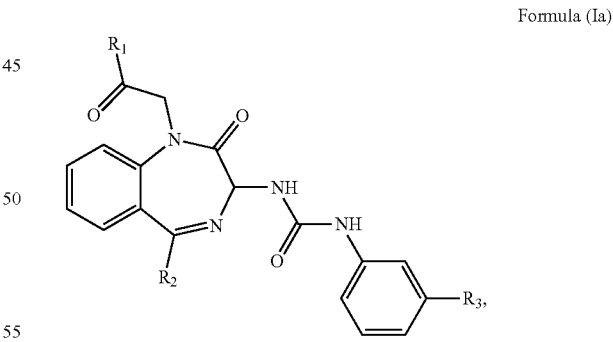

Formula (Ia)

wherein R1 and R2 are independently a hydrogen atom, a substituted or unsubstituted linear or branched chain C1 to C5 alkyl group, a substituted or unsubstituted aryl group, or a heteroaryl; and R3 is a hydrogen atom, a substituted or unsubstituted linear or branched chain C1 to C3 alkyl group, or a C1 to C3 alkylamino group.

2. The method of claim 1, wherein the cholecystokinin-2 receptor antagonist has a structure of Formula (Ia) with $R_1$ being a linear or branched chain C1 to C4 alkyl group, or a substituted or unsubstituted aryl group; $R_2$ being a substituted or unsubstituted aryl group, or a heteroaryl; and R₃ being a methyl group, an ethyl group, a methylamino group or an ethylamino group.

3. The method of claim 1, wherein the cholecystokinin-2 receptor antagonist has a structure of Formula (IIa) or Formula (IIIa):

Formula (IIa)

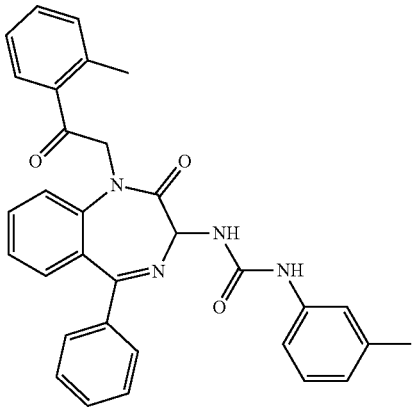

Formula (IIIa)

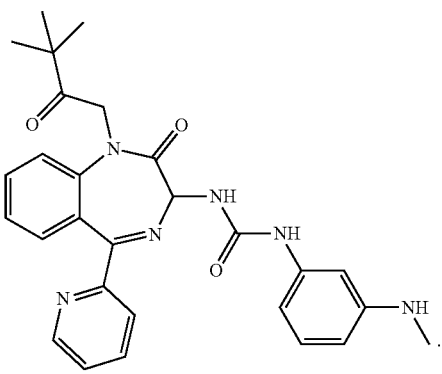

4. The method of claim 1, wherein the cholecystokinin-2 receptor antagonist has a structure of Formula (IIb) or Formula (IIIb):

Formula (IIb)

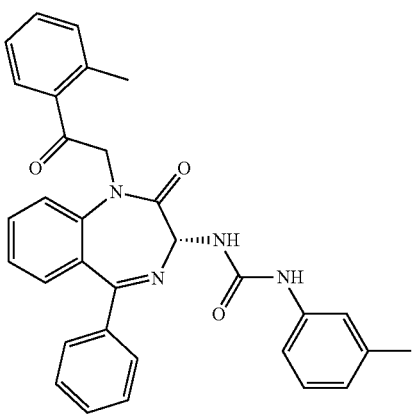

Formula (IIIb)

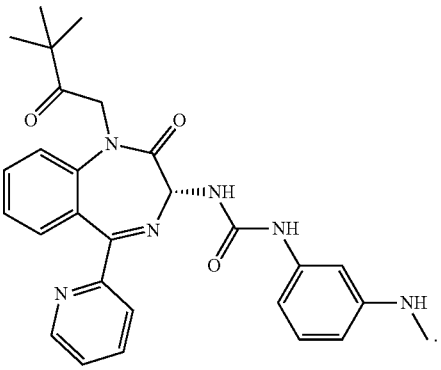

5. The method of claim 1, wherein the mental disorder is depression.

6. The method of claim 1, wherein the cholecystokinin-2 receptor antagonist is administered in combination with one or more antidepressant compounds to the subject.

7. The method of claim 6, wherein the antidepressant compound is selected from the group consisting of citalopram, escitalopram, paroxetine, fluoxetine, sertraline, selegiline, isocarboxzaid, parnate, tranylcypromine, imitriptyline, amoxapine, desipramine, doxepin, imipramine, nortriptyline, protriptyline, trimipramine, maprotiline, trazodone, nefazodone, mirtazapine, bupropion, venlafaxine, duloxetine, and desvenlafaxine.

8. The method of claim 1, wherein the cholecystokinin-2 receptor antagonist is administered to the subject via injection.

9. A pharmaceutical composition comprising a cholecystokinin-2 receptor antagonist or a pharmaceutical acceptable salt thereof as an active ingredient, one or more antidepressant compounds, and optionally a pharmaceutically acceptable excipient, wherein the cholecystokin-2 receptor antagonist has a structure of Formula (Ia):

Formula (Ia)

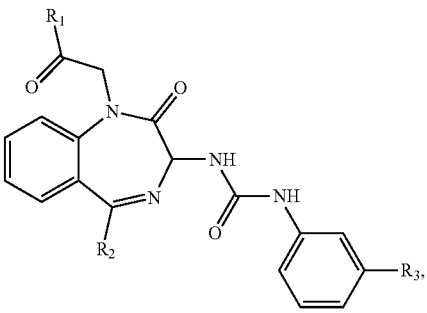

wherein $R_1$ and $R_2$ are independently a hydrogen atom, a substituted or unsubstituted linear or branched chain C1 to C5 alkyl group, a substituted or unsubstituted aryl group, or a heteroaryl; and
$R_3$ is a hydrogen atom, a substituted or unsubstituted linear or branched chain C1 to C3 alkyl group, or a C1 to C3 alkylamino group.

10. The pharmaceutical composition of claim 9, wherein the cholecystokinin-2 receptor antagonist has a structure of Formula (Ia) with $R_1$ being a linear or branched chain C1 to C4 alkyl group, or a substituted or unsubstituted aryl group;

R₂ being a substituted or unsubstituted aryl group, or a heteroaryl; and R₃ being a methyl group, an ethyl group, a methylamino group or an ethylamino group.

11. The pharmaceutical composition of claim 9, wherein the cholecystokinin-2 receptor antagonist has a structure of Formula (IIa) or Formula (IIIa):

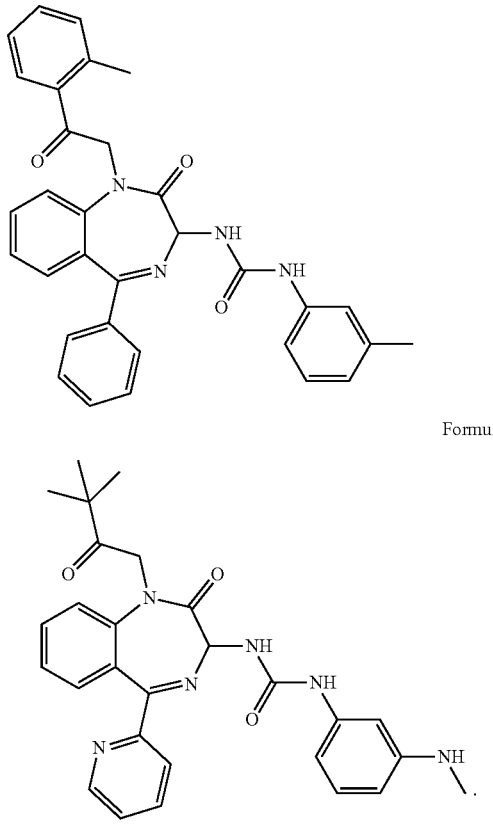

Formula (IIa)

Formula (IIIa)

12. The pharmaceutical composition of claim 9, wherein the cholecystokinin-2 receptor antagonist has a structure of Formula (IIb) or Formula (IIb):

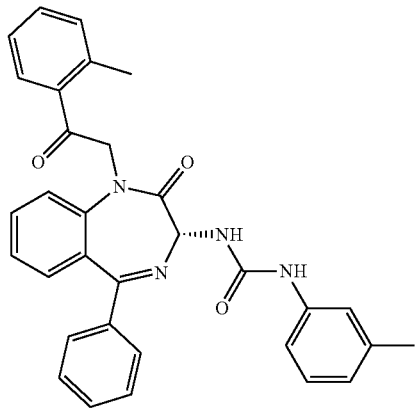

Formula (IIb)

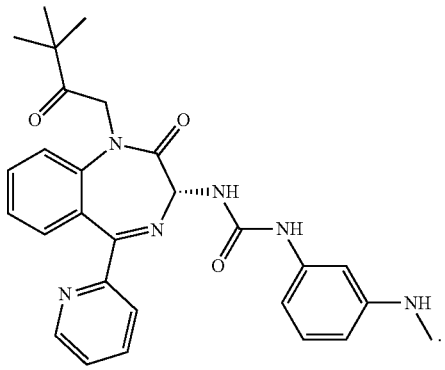

Formula (IIIb)

13. The pharmaceutical composition of claim 9, wherein the antidepressant compound is selected from the group consisting of primidone, diazepam, perampanel, tiagabine, methsuximide, ethosuximide, stiripentol, phenobarbital sodium, felbamate, acetazolamide, brivaracetam, benzobarbital, phenytoin sodium, clobazam, fosphenytoin sodium, ezogabine, lacosamide, eslicarbazepine, topiramate, oxcarbazepine, zonisamide, lamotrigine, carbamazepine, clonazepam, vigabatrin, levetiracetam, divalproex sodium, valproic acid, lorazepam, clorazepate, and gabapentin.

* * * * *